US006458762B1

(12) United States Patent
McKenzie et al.

(10) Patent No.: US 6,458,762 B1
(45) Date of Patent: Oct. 1, 2002

(54) THERAPEUTIC USE OF HEMOGLOBIN FOR PRESERVING TISSUE VIABILITY AND REDUCING RESTENOSIS

(75) Inventors: Jack E. McKenzie, McLean, VA (US); Kenneth E. Burhop, Mundelein, IL (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 08/350,204

(22) Filed: Dec. 2, 1994

Related U.S. Application Data

(63) Continuation-in-part of application No. 08/218,536, filed on Mar. 28, 1994, now abandoned.

(51) Int. Cl.$^7$ .......................... A61K 38/16; A61K 35/14
(52) U.S. Cl. ............................................ 514/6; 530/385
(58) Field of Search ............................ 514/6; 530/385

(56) References Cited

U.S. PATENT DOCUMENTS

| | | | |
|---|---|---|---|
| 4,053,590 A | 10/1977 | Bonsen et al. | |
| 4,055,635 A | 10/1977 | Green et al. | |
| 4,061,736 A | 12/1977 | Morris et al. | |
| 4,336,248 A | 6/1982 | Bonhard et al. | |
| 4,529,719 A | * 7/1985 | Tye ............................... | 514/6 |
| 4,600,531 A | 7/1986 | Walder | |
| 4,640,835 A | 2/1987 | Shimizu et al. | |
| 4,740,594 A | 4/1988 | Mauzac et al. | |
| 4,757,052 A | 7/1988 | Markov | |
| 4,826,811 A | 5/1989 | Sehgal et al. | |
| 4,866,096 A | 9/1989 | Schweighardt | |
| 4,873,230 A | 10/1989 | Belzer et al. | |
| 4,935,465 A | 6/1990 | Garman | |
| 4,988,515 A | 1/1991 | Buckberg | |
| 4,994,444 A | 2/1991 | Zikria | |
| 5,084,558 A | 1/1992 | Rausch et al. | |
| 5,194,590 A | 3/1993 | Sehgal et al. | |
| RE34,271 E | 6/1993 | Walder | |
| 5,248,785 A | 9/1993 | Abraham et al. | |
| 5,268,500 A | 12/1993 | Lalezari et al. | |
| 5,296,465 A | 3/1994 | Rausch et al. | |
| 5,306,508 A | 4/1994 | Kossovsky et al. | |
| 5,334,706 A | 8/1994 | Przybelski | |
| 5,370,870 A | 12/1994 | Wong | |
| 5,386,014 A | 1/1995 | Nho et al. | |
| 5,428,007 A | 6/1995 | Fischer et al. | |
| 5,432,191 A | 7/1995 | Abraham et al. | |
| 5,464,814 A | 11/1995 | Sehgal et al. | |
| 5,510,464 A | 4/1996 | Przybelski | |
| 5,514,780 A | 5/1996 | Dellacherie et al. | |

FOREIGN PATENT DOCUMENTS

| | | |
|---|---|---|
| AU | 622610 | 4/1992 |
| CA | 1312009 | 12/1992 |
| CA | 2074852 | 1/1994 |
| EP | 0140640 | 5/1985 |
| EP | 0361719 | 9/1989 |
| EP | 0361720 | 4/1990 |
| EP | 0446699 | 9/1991 |
| EP | 0277289 | 4/1992 |
| FR | 2551660 | 3/1985 |
| FR | 2640141 | 6/1990 |
| WO | 8404248 | 11/1984 |
| WO | 8707832 | 12/1987 |
| WO | 8803408 | 5/1988 |
| WO | 9308842 | 5/1993 |
| WO | 9316720 | 9/1993 |

OTHER PUBLICATIONS

Lutz et al., "Oxygen Transport to Tissues XII", 1990, pp. 683–690.*

Kim et al, "Effects of Hemoglobin . . . ", Biomat. Art. Cells. Artif. Organs., vol. 16., Nos. 1–3, 331–345, 1988.*

Yamakawa et al, "Effects of Pyridoxalated Hemoglobin . . . ", Artif Organs 14 (3) , 1990.*

Amberson et al. On the Use of Ringer Locke Solutions Containing Hemoglobin as a Substitute for Normal Blood in Mammals Journal of Cellular and Comparative Physiology, vol. 5, pp. 359–382, 1934.

Amberson et al. Clinical Experience with Hemoglobin–Saline Solutions Journal of Applied Physiology, vol. I, No. 7, pp. 469–489, 1949.

Biro et al. Coronary Vascualr Actions of Stroma–Free Hmoglobin Preparations Artificial Organs, vol. 12, No. 1, pp. 40–50, 1988.

Biro et al. The Effect of Hemodilution with Stroma–Free Hemoglobin and Dextran on Collateral Perfusion of Ischemic Myocardium in the Dog Amercan Heart Journal, vol. 99, No. 1, pp. 67–75, 1980.

Block et al. Morphology After Transluminal Angioplasty in Human BeingsHematologic Effects of Hemoglobin Solutions in Anima The New England Journal of Medicine, vol. 305, No. 7, pp. 382–385, 1981.

Capparelli et al. Diltiazem Improves Resuscitation from Experimental Ventricular Fibrillation in Dogs Critical care Medicine, vol. 20, No. 8, pp. 1140–1145, 1992.

Chow et al. Effect of Exernal Cardiopulmonary Resuscitation on Lidocaine Pharmacokinetics in Dogs The Journal of Pharmacology and Experimental Therapeutics, vol. 224, No. 3, pp. 531–537, 1983.

Cocks et al. Oxyhaemoglobin Increases the Production of Endothelin–1 by Endothelial Cells in Culture European Journal of Pharmacology, vol. 196, pp. 177–182, 1991.

(List continued on next page.)

Primary Examiner—Deborah C. Lambkin
(74) Attorney, Agent, or Firm—Senniger, Powers, Leavitt & Roedel

(57) ABSTRACT

Administration of low doses of hemoglobin minimizes damage to the myocardium after blockage and significantly reduces reperfusion injury. Hemoglobin exerts a pharmacological effect by increasing perfusion and blocking the molecular events leading to permanent injury following an ischemic episode. Additional benefits include a reduction in the number of post-ischemic arrhythmias, reduction in the incidence of restenosis, and improved contractile function in the area of risk.

35 Claims, 4 Drawing Sheets

OTHER PUBLICATIONS

Coetzee et al. Halothane and the Reperfusion Injury in the Intact Animal Model Anesth. Analg., vol. 76, No. 4, pp. 734–744, 1993.

Cole et al. Focal Cerebral Ischemia in Rats: Effect of Hemodilution with x–x Cross–Linked Hemoglobin on Brain Injury and Edema The Canadian Journal of Neurological Sciences, vol. 20, No. 1, pp. 30–36, 1993.

Cole et al. Hemodilution during Cerebral Ischemia in Rats: Effects of Stroma–Free Hemoglobin on Brain Injury Anseth. Analog, vol. 74, Abstract S50, 1992.

Elger et al. Magnetic Resonance Imaging Study on the Effect of Levemopamil on the Size of Intracerebral Hemorrhage in Rats Stroke, vol. 25, No. 9, pp. 1836–1841, 1994.

Estep Efficacy and Safety of a Diaspirin Modified Hemoglobin Solution ISBT Presentation, 1988.

Feola et al. Improved Oxygenation of Ischemic Myocardium by Hemodilution with Stroma–Free Hemoglobin Solution Chest, vol. 75, No. 3, pp. 369–375, 1979.

Foley et al. Cytotoxic Effects of Bloody Cerebrospinal Fluid on Cerebral Endothelial Cells in Culture Journal of Neurosurgery, vol. 81, pp. 87–92, 1994.

Forster et al. The Use of Stroma–Free Hemoglobin Solutions as Blood Substitute Infusionsther Klin Ernahr., vol. 4, No. 2, pp. 122–126, (abstract), 1977.

Greenburg et al. Intravascular Persistence and Oxygen Delivery of Pyridoxalated, Stroma–Free Hemoglobin During Gradations of Hypotension Surgery, vol. 86, No. 1, pp. 13–16, 1979.

Halstenson et al. Pharmacologic Profile of Diaspirin Cross–linked Hemoglobin (DCLHb) in Hemodialysis (HD) Patients Journal of American Society of Nephrology, vol. 5, No. 3, Abstract 84P, pp. 451, 1994.

Hariman et al. Regional Changes in Blood Flow, Extracellular Potassium and Conduction During Myocardial Ischemia and Reperfusion. JACC, vol. 21, No. 1, pp. 798–808, 1993.

Hauck et al. Intracoronary Diaspirin Crosslinked Hemoglobin (DCLHb) Infusion During Coronary Balloon Occlusion in Dogs and Pigs Abstract–Biomaterials, Artificial Cells, and Immobilization Biotechnology, vol. 19, No. 2, 1991.

Jakobsen Brain Ischemia In Subarachnoid Hemorrhage pp. 3–32, 1992.

Jan et al. Coronary Hemodynamics and Oxygen Utilization After Hematocrit Variations in Hemorrhage Am. J. Physiol., vol. 239, pp. H326–H332, 1980.

Jennings et al. Referfusion Injury, Definitions and Historical Background Myocardial Protection: the Pathophysiology of Reperfusion and Reperfusion Injury, pp. 1–11, 1992.

Jeroudi et al. Myocardial Reperfusion Injury: Role of Oxygen Radicals and Potential Therapy with Antioxidants The American Journal of Cardiology, vol. 73, pp. 2B–7B, 1994.

Kim et al. Coagulation Function After In–Vitro Hemodilution With Hemoglobin Solution Aftificial Cells Blood Substitutes and Immobolization Biotech., vol. 22, No. 3, pp. 613–618, 1994.

Kim et al. Effects of Hemoglobin Perfusion of Contractile Function of the Isolated Ventricular Septa Biomat. Art. Cells, Art. Org., vol. 16, Nos. 1–3, 331–345, 1988.

Kloner Does Reperfusion Injury Exist in Humans? J. Am. Coll. Cardiol., vol. 21, No. 2, pp. 537–545, 1993.

Lie et al. The Reasons Why Clinical Cardiologists Disregard Reperfusion Arrhythmias Cardiovascular Research, vol. 27, p. 1906, 1993.

Linz et al. Effects of Diaspirin Crosslinked Hemoglobin (DCLHb) During Coronary Ischemia/Reperfusion in the Swine Cardiovascular Research, vol. 28, No. 8, pp. 88–92, 1994.

Liu et al. Reduction of Postischaemic Ventricular Dysfunction and Arrhythmias by Trapping Hydroxyl Radicals with Salicylic Acid Int. J. Tiss. Reac., vol. 15, No. 1, pp. 25–30, 1993.

Marks Hemoglobin Solution Effects on the Heart Letterman Army Institute of Research, Report No. 219, 1986.

Messmer et al. Oxygen Supply to the Tissues During Limited Normovolemic Hemodilution Res. Exp. Med., vol. 159, pp. 152–166, 1973.

Messmer et al. Present State of Intentional Hemodilution Eur. Surg. Res., vol. 18, pp. 254–263, 1986.

McKenzie et al. Effects of Diasprin Cross–linked Hemoglobin (DCLHb) on Cardiac Function and ECG in the Swine Biomater. Artif. Cells Immob. Biotech., vol. 20, No. 2–4, pp. 683–687, 1992.

McKenzie et al. Effects of Diasprin Cross–linked Hemoglobin (DCLHb) on Cardiac Function and ECG in the Swine FASEB Journal, vol. 5, No. 5, Abstract No. 1897, 1991.

McKenzie et al. Effects of Diaspirin Crosslinked Hemoglobin During Coronary Angioplasty in the Swine Cardiovascular Research, vol. 28, No. 8, pp. 1188–1192, 1994.

Origitano et al. Sustained Increased Cerebral Blood Flow with Prophylactic Hypertensive Hypervolemic Hemodilution ("Triple–H" Therapy) after Subarachnoid Hemorrhage Neurosurery, vol. 27, No. 5, pp. 729–740, 1990.

Otani et al. Reperfusion Injury Induced by Augmented Oxygen Uptake in the Initial Reperfus ion Period Possible Efficacy of Extreme Hemodilution J. Mol. Cell. Cardiol., vol. 17, No. 5, pp. 457–466, 1985.

Pohl et al. Endothelium–dependent Modulation of Vascular Tone and Platelet Function European Heart Journal, vol. 11, Supplement B, pp. 35–42, 1990.

Rebello et al. Diaspirin Crosslinked Hemoglobin Reverses the Reduction in Cerebral Blood Flow Induced by Central Endothelin (ET) The FASEB Journal, vol. 8, No. 4, Part II, Abstract No. 4802, pp. A828, 1994.

Riess Flourocarbon–Based in vivo Oxygen Transport and Delivery Systems Vox Sang, 61: pp. 225–239, 1991.

Schell et al. Hemodilution During Cerebral Ischemia in Rats: Effects of Stroma–Free Hemoglobin on Blood Flow Anesth Analog, vol. 74, Abstract S262, 1992.

Schell et al. Hemodilution with Diaspirin Hemoglobin During Cerebral Ischemia in Rats: The Effect on Cerebral Blood Flow.

Sheeman et al. Advantages and Applications of the Centerline Method for Characterizing Regional Ventricular Function Circulation, vol. 74, No. 2, pp. 293–305, (abstract), 1986.

Sheeman et al. Measurement of Regional Wall Motion from BiPlane Contract Ventriculograms: A Comparison of the 30 Degree Right Anterior Oblique & 60 Degree Left Anterior Oblique & 60 Degree left Anterior Oblique Projections in Circulation, vol. 74, No. 4, pp. 796–804, (abstract), 1986.

Siesjo Pathophysiology and Treatment of Focal Cerebral Ischemia. Part I: Pathophysiology Journal of Neurosuregery, vol. 77, pp. 169–184, 1992.

Siesjo Pathophysiology and Treatment of Focal Cerebral Ischemia. Part II: Mechanisms of Damage and Treatment Journal of Neruosuregery, vol. 77, pp. 337–354, 1992.

Sujov et al. Systemic Hemodynamics and Regional Circulatory Effects of Centrally Administered Endothelin (ET) FASEB Journal, vol. 8, No. 4, Abstract 1926, pp. A333, 1994.

Thornton et al. Coumadin and Aspirin in Prevention of Recurrence After Transluminal Coronary Angioplasty: A Randomized Study Coronary, vol. 69, No. 4, pp. 721–727, 1984.

Tran et al. Effect of Diaspirin Crosslinked Hemoglobin (H) on Ventricular Fibrillation Threshold (VFT) and Acid–Based Status During Cardiopulmonary Resuscitation (CPR).

Wilson et al. The Use of Arterial–Central Venous Oxygen Differences to Calculate Cardiac Output and Oxygen Consumption in Critically Ill Surgical Patients Surgery, vol. 84, No. 3, pp. 362–369, 1978.

Wyngaarden et al. Cecil Textbook of Medicine, 19th Edition, vol. 2, Selected pp. 2162–2165, 1992.

Yellon et al. Myocardinal Protection: The Pathophysiology of Reperfusion and Reperfusion Injury Chemical Abstracts, Abstract No. 12626lt, vol. 116, No. 13, p. 640, 1992.

Zikria et al. A Biophysical Approach to Capillary Permeability Surgery, vol. 105, No. 5, pp. 625–631, 1989.

Zikria et al. Hydroxyethyl Starch Macromolecules Reduce Myocardial Reperfusion Injury Arch Surgery, vol. 125, pp. 930–934, 1990.

* cited by examiner

THERAPEUTIC USE OF HEMOGLOBIN FOR PRESERVING TISSUE VIABILITY AND REDUCING RESTENOSIS

CROSS REFERENCE TO RELATED APPLICATION

This is a continuation-in-part of U.S. patent application No. 08/218,536 filed Mar. 28, 1994.

BACKGROUND OF THE INVENTION

The blockage of an arterial vessel produces ischemia in the tissue normally nourished by the occluded vessel. If the blockage is removed permitting reperfusion of the affected area after greater than sixty minutes of ischemia, further injury, called reperfusion injury, is paradoxically observed. This reperfusion injury is associated with a number of biochemical and physiological events such as release of intracellular enzymes, transient rise in blood pressure, reduction in contractility, influx of calcium, disruption of cell membranes, and eventual tissue necrosis (see Ferrari, et al., *Am. J. Clin. Nutr.* 53:2158 (1991)). It is thought that much of the tissue damage arising during ischemia and reperfusion results from the chemical action of excess amounts of accumulated oxygen free radicals (Lefer, et al., *Basic Res. Cardiol.,* 86 Suppl. 2:109 (1991); Kirsh, et al., *J. Neurotrauma,* 9 Suppl. 1:S157 (1992); and Bolli, *Cardiov. Drugs & Ther.,* 5:249 (1991)).

Experiments in a number of animal models have investigated the use of antioxidants or enzymes to control reperfusion injury. For example, Weyrich, et al., *Circulation,* 86:279 (1992) showed that administration of L-arginine reduced necrotic injury in a cat model of myocardial infarction. McMurray et al., *J. Clin. Pharmac.,* 31:373 (1991) investigated sulfhydryl containing angiotensin converting enzyme inhibitors. Naslund, et al., *Circ. Res.,* 66:1294 (1990) concluded from their work on a swine coronary model, that infarct size could be limited by administration of superoxide dismutase, but only during a very narrow window of time post-infarction. Schaer, et al., *JACC,* 15:1385 (1990) report a reduction in reperfusion injury by administering an acellular oxygenated perfluorochemical emulsion called Fluosol.

An important model system is percutaneous transluminal coronary angioplasty in the pig. McKenzie, et al., *Cardiovascular Research*, "Effects of diaspirin cross-linked hemoglobin during coronary angioplasty in the swine", 28(8):1188–1193 (1994) utilized this technique to study the effects of temporary regional myocardial ischemia. They inserted a catheter into the proximal left anterior descending coronary artery and inflated the catheter balloon to occlude the artery for a period of 4 minutes. A significant reduction in cardiac function compared to controls was observed as measured by mean arterial blood pressure (MAP), peak systolic left ventricular pressure (IVP), rate of left ventricular pressure development (dP/dt), pressure rate product (PRP), and cardiac output (CO). In addition, electrocardiograms showed elevation of the S-T segment of the ECG. These experiments are significant because McKenzie, et al. compared controls to animals receiving infusions of hemoglobin, and found that cardiac function increased significantly and the S-T segment of the ECG returned toward baseline.

The concept of infusing hemoglobin products as a substitute for blood has a long history (for a historical perspective, see R. M. Winslow, "Hemoglobin-based Red Cell Substitutes", *The Johns Hopkins University Press,* 1992). Free hemoglobin is not suitable for this purpose since oxygen is bound too tightly to be released in the tissues. Also, hemoglobin monomers are rapidly cleared from the blood and exhibit renal toxicity. Better success has been achieved with chemically modified hemoglobins, which assume a conformation allowing release of oxygen, and whose size and stability are more resistant to clearance.

Hemoglobins may be alpha alpha cross-linked as disclosed in U.S. Pat. No. 4,600,531 and RE 34,271 (Walder), and virus inactivated and purified as taught in U.S. Pat. No. 4,831,012 (Estep). Modification by pyridoxyation, carbamylation, or carboxymethylation is also known, as are chemical schemes for both cross-linking and polymerizing, as by glutaraldehyde. A summary of these chemistries is contained in Winslow, supra.

SUMMARY OF THE INVENTION

This invention provides a method for treating blockage of a blood vessel, which may be a thrombus, fat embolus, plaque, or other obstruction, or restenosis at remote times of a previously blocked vessel, which comprises administering, generally by intravenous infusion, hemoglobin to a patient undergoing tissue ischemia. There are different ways of defining the therapeutically efficacious dose which may be administered. An amount of hemoglobin may be administered which is sufficient to suppress or reduce reperfusion injury to the tissue whose nourishment has been disrupted by the blockage. These doses are effective not only to delimit the amount of infarcted tissue as a percentage of the cardiac tissue at risk during occlusion, but also for preventing restenosis of the vessel after the original blockage has been relieved. This protection effect is also measured by the reduction in number, magnitude, and duration to onset of ventricular arrhythmias which are known to precipitate sudden cardiac arrest in a significant proportion of patients suffering myocardial infarction. This protection is further measured by improved regional myocardial function in the border zone. Thus, the present invention affords a method for improving contractile function in ischemic cardiac tissue following relief of heart vessel blockage comprising administering hemoglobin in a dose effective to obtain a wall motion score improvement of at least 0.15 relative units between the infarct zone and 20 chords in the tissue region at risk. An effective amount is in the range of 10–2500 mg/kg of body weight, preferably 75–750 mg/kg.

The present invention thus provides a method of reducing the frequency and duration to onset of cardiac arrhythmias following relief of cardiac arterial blockage by administering hemoglobin generally in a like dose. This method also results in reducing the incidence of restenosis of a blood vessel at remote times after relief of a blockage thereof by administering hemoglobin in a like dose, which generally falls within the range of 10–2500 mg/kg of body weight, preferably 75–750 mg/kg.

The benefits and objects of administering hemoglobin as a treatment for blood vessel blockage are that it increases salvage of the area at risk, it stabilizes the circulatory system, as in cardiac ischemia, and may act directly or indirectly to lower levels of free oxygen radicals and other molecular species associated with tissue damage. It also ameliorates injury to an occluded vessel associated with restenosis of the vessel at remote times up to several weeks or longer. Many of hemoglobin's pharmacological properties are not yet understood mechanistically. It would appear that some of these properties are unrelated to oxygen-delivery since the effects are exerted at hemoglobin doses which are too low to make a significant impact on this parameter.

DETAILED DESCRIPTION OF THE PREFERRED EMBODIMENT

Figure 1A:
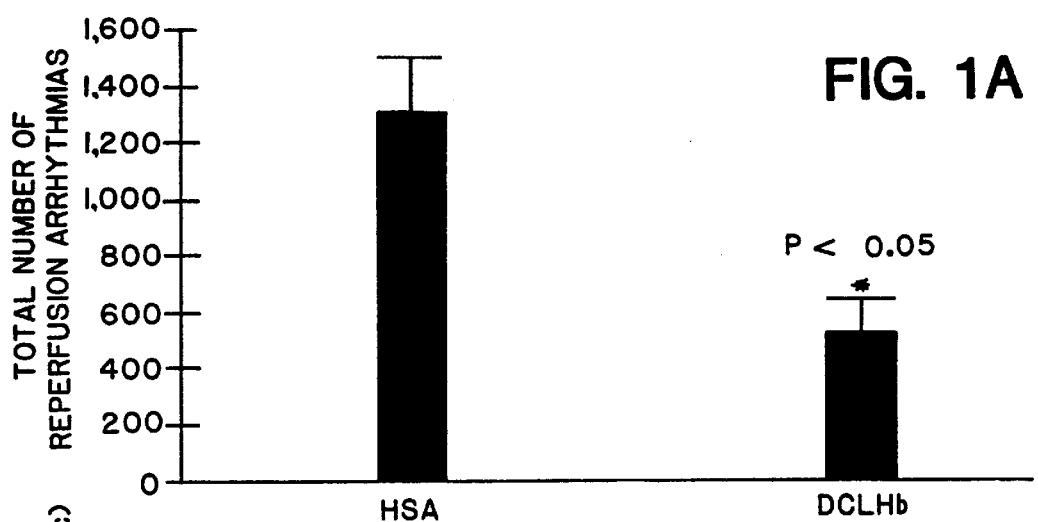
FIG. 1A. Effects of human serum albumin (HSA) and diaspirin cross-linked hemoglobin (DCLHb™) on the total number of reperfusion arrhythmias. The number of arrhythmias are counted from beginning of reperfusion for 45 minutes. Values are means±SEM. *Significantly different from HSA (P<0.05).

The blockage of blood vessels may occur by any one of several mechanisms including degenerative plaque, thrombosis, fat embolus, or blood clot, and may occur in many tissues and locations of the body. The effect of such blockage is to impair or completely curtail blood flow to the portions of the vessel downstream from the blockage. The tissue nourished by the occluded vessel is thus deprived of oxygen and nutrients, and cell death may ensue. In situations where the affected vessel is a coronary artery or an artery which serves a vital brain or other organ function, the blockage may be life-threatening.

Reperfusion therapy utilizing hemoglobin is effective when some degree of blood flow is restored, or in situations in which collateral blood flow can take advantage of the increase in perfusion resulting from hemoglobin administration. Where occlusion of the blood vessel is essentially complete, restoration of flow may occur spontaneously, may be restored by administration of thrombolytic enzymes such as streptokinase or tissue plasminogen activator, or by surgical intervention or angioplasty.

The dosage of hemoglobin utilized in reperfusion therapy varies from patient to patient, but generally will fall in the range from 10 to 2500 mg/kg of body weight. While hemoglobin acts to increase perfusion as indicated by increased blood flow, in some indications it does not appear to act by this mechanism in cardiac reperfusion. However, low doses in the range from 75 to 750 mg/kg of body weight are generally preferred and are efficacious pharmacologically. The dramatic limiting of reperfusion injury and consequent reduction of permanent. cell damage in the area at risk cannot presently be fully explained, and Applicants therefore do not wish to be bound to any particular theory.

Ideally, a physician will administer an amount of hemoglobin which confers the desired effect of optimally suppressing reperfusion injury, thereby preserving tissue viability after blockage, and minimizing permanent cellular damage. Suppressing reperfusion injury has indirect benefits in addition to limiting tissue damage in the region at risk. For a review of reperfusion injury, refer to the book by Jennings and Yellon, Myocardial Protection: The Pathophysiology of Reperfusion and Reperfusion Injury (Raven Press, Ltd., N.Y. (1992) As shown in Example 1, use of hemoglobin results in a prolongation in the time at which cardiac arrhythmias arise, and lowers their frequency. Thus hemoglobin administration provides a method of reducing the frequency of ventricular arrhythmias, and in turn preventing cardiac arrest.

Another indirect benefit of hemoglobin administration is in preventing or reducing the incidence of restenosis. It is a not infrequent complication of angioplasty and surgical bypass techniques, that when the occlusion is relieved restenosis readily occurs. This may occur within minutes or hours after relief of the blockage, or at remote times of several weeks or longer. Thus, the unblocking procedures must be repeated, or the patient eventually succumbs because the same vessel whose blockage was relieved, has again become occluded. It is believed that residual damage to the vessel walls may attract cellular blood constituents, which adhere to the vessel lumen and initiate arteriosclerotic deposition. Surprisingly, after infusion of hemoglobin following relief of blockage statistically fewer vessels restenose than is observed in control groups. It is also observed that wall motion in the region adjacent to the infarct zone is dramatically improved in hemoglobin treated vs. HSA treated animals. Thus, the present invention provides a method for reducing restenosis in blood vessels from which occlusion has been relieved. This amount has been determined empirically as falling within 10 and 2500 mg/kg of body weight. As a practical matter, the physician can administer hemoglobin in increments until the mean arterial blood pressure has attained a value about 5 to 15 percent above the hemoglobin preadministration baseline. Applicants now understand that an increase in perfusion and the well-known pressor effect of hemoglobin are not necessarily causally linked, because suppression of the pressor effect by drugs such as prazosin does not impair the observed increase in perfusion.

The timing of administration should preferably be at a time just prior to relief of the blockage and reperfusion. Ideally this should be within 20 minutes of relief of blockage. However, treatment out to 1 hour prior to or after the relief of blockage may be beneficial, particularly when the blood vessel involved impacts a relatively small area at risk. In the case of cardiac blockage, a relatively small area at risk would involve about 5 to 25 percent of the myocardium.

The hemoglobin utilized in reperfusion therapy may be any type which has the following general properties: stroma-free, non-antigenic and non-pyrogenic (i.e. less than 0.25 endotoxin units per milliliter), and be free of bacterial and viral contamination. The hemoglobin may be isolated as disclosed in U.S. Pat. Nos. 4,439,357, 4,526,715, 4,598,064, and 4,600,531 hereby incorporated by reference. The hemoglobin is preferably rendered virus free, as disclosed in U.S. Pat. No. 5,281,579, incorporated by reference.

The preferred hemoglobin is maintained in stable oxygen-releasing conformation by cross-linking. The best method of cross-linking involves a lysine-lysine bridge between the alpha subunits, as disclosed in U.S. Pat. No. 4,600,531 and RE 34,271. Because the tetramer cannot fall apart, thereby retaining its 64,000 molecular weight, clearance from the blood stream is slowed. Further lengthening of blood retention time is effected by polymerizing the hemoglobin tetramers, as by polyamide linking groups disclosed in co-owned U.S. application Ser. No.08/173,882. Alternative cross-linking and polymerizing techniques are described in Winslow, supra. One interesting technique involves simultaneous cross-linking and polymerizing with glutaraldehyde as disclosed in U.S. Pat. No. 5,194,590.

Other advantages of the present invention will be apparent from the Examples, which follow.

EXAMPLE 1

An animal model system involving coronary occlusion was used to study the effect of hemoglobin perfusion therapy on controlling tissue damage resulting from sustained ischemia and reperfusion injury. The swine model is the model of choice because numerous studies have shown that the pig heart most closely resembles the human heart physiologically. For a review, see M. M. Swindle, ed., "Swine as Models in Biomedical Research", *Iowa State University Press*, (1992).

One particularly important criterion is the comparable absence in both the pig and humans of collateral flow. Collateral flow is the ability of the capillary bed of one arterial branch to compensate for an occlusion in another branch. The pig heart most closely resembles the human heart in showing a low degree of collateral flow capacity. See Bloor, et al., "The Pig as a Model of Myocardial Ischemia and Gradual Coronary Artery Occlusion", in *Swine as Models in Biomedical Research*, supra.

Experimental Preparation. Yorkshire swine of either sex (n=15), weighing 21.3±1.4 kg, were initially sedated with Ketamine (10 mg/kg, i.m.) to allow placement of an intravenous catheter in an ear vein. Anesthesia was obtained with Pentobarbital Sodium (Nembutal) 30 mg/kg, bolus i.v. injection, with a dose of 31.5 mg/hour given by continuous i.v. infusion, at a rate of 6.3 ml/hour (Sage Instruments Pump), to maintain a surgical plane of anesthesia. The swine were intubated and ventilated (Harvard Respirator). Respiratory status was monitored periodically with arterial blood gas determinations and ventilation rate and/or oxygen flow rate were adjusted to achieve physiological blood gas values. Bilateral femoral cutdowns were performed and the right femoral artery was cannulated with a 9F sheath (Cordis) and a 6F pigtail catheter was advanced under fluoroscopic guidance into the left ventricle. A right carotid cutdown was performed and the right carotid artery was cannulated with a 9F sheath. Three thousand units of Heparin sodium were administered intravenously and repeated doses of 1,000 units were given every 30 minutes. A bolus of 1 mg/kg of lidocaine was given i.v. and an infusion of 50 $\mu$g/kg/min was maintained throughout the experiment. Intravenous nitroglycerine was infused to achieve a 5–10 mmHg reduction in blood pressure during guide wire and balloon placement but was discontinued prior to balloon inflation. Electrocardiograph, blood pressure, and temperature monitoring was performed throughout the experiment.

A 7F AR2 guiding catheter (Scimed) was advanced to the left main coronary artery. Catheter position was confirmed and angiograms were performed using hand injections of 1–5 cc of iodinated contrast (Renografin-76). A 0.014 inch Hi-Torque floppy guide wire (Advanced Cardiovascular Systems) was advanced into the first obtuse marginal branch of the circumflex coronary artery. A Hartzler ACX II® (2 mm diameter, 10 mm length) balloon angioplasty catheter (Advanced Cardiovascular Systems) was advanced over the guide wire into the first marginal branch. Care was taken to assure that the balloon did not obstruct flow in the main circumflex coronary artery. The balloon was inflated with just enough pressure to insure complete occlusion (2–4 ATM) of the first marginal branch for 90 minutes. Occlusion was confirmed by angiography.

Study Protocol. Prior to instrumentation the swine were randomized into one of two study groups. Ten minutes prior to balloon deflation the swine were intravenously infused at 5 ml/kg given over a five minute period (1 ml/kg/min) with either 10% diaspirin cross-linked hemoglobin (DCLHb™) or a Human Serum Albumin (HSA) solution which was oncotically matched to the hemoglobin solution (approximately 8% albumin). At ninety minutes the balloon was deflated and withdrawn. The animal was then allowed to reperfuse for 3 hours. An angiogram was performed after the 3 hour reperfusion period to document vessel patency. The animals were euthanized and the hearts rapidly removed.

ECG Recording. All pigs were instrumented with leads I, II, III, aVr, aVl, aVf, and the precordial lead $V_4$. The total number of arrhythmias were counted from the start of reperfusion to 45 minutes post-reperfusion. The time to onset of arrhythmias was measured from start of reperfusion to the onset of reperfusion arrhythmias. The total duration of the reperfusion arrhythmic period was calculated as the amount of time from the onset of reperfusion arrhythmias to a time point when the arrhythmias occurred less than one every 30 seconds. S-T segment changes following balloon occlusion were recorded from the isoelectric line either following the P or the T wave from the standardized precordial lead $V_4$.

Myocardial blood flow. Myocardial blood flow was measured using radioactive microspheres. Microspheres were injected at baseline, 60 minutes after occlusion, 5 minutes after the initiation of reperfusion and after 170 minutes of reperfusion. The radioactive microspheres were supplied as carbonized plastic spheres 15.5±3.0 microns in diameter, which were labeled with either $^{153}$Gd, $^{85}$Sr, $^{46}$Sc, or $^{113}$Sn. The isotope is bonded into the carbonized plastic and does not leach from the sphere in saline or plasma. Microspheres (New England Nuclear) were obtained as 1 mCi of nuclide in 10 ml saline, to which 0.05% Tween-80, a surface detergent, was added to minimize aggregation. Twenty $\mu$Ci of the microspheres were removed from the sterile sealed vial with a syringe and diluted in saline to the appropriate concentration. The order of the microsphere injection was randomized to avoid bias of the data from microsphere lot or isotope type. The mixture of spheres was sonicated for at least 30 minutes prior to injection to assure complete dispersal. Immediately before injection, the microspheres were mechanically shaken with a Vortex type mixer. Approximately $1.3 \times 10^6$ microspheres were injected into the left ventricle and flushed with saline. In theory, the microspheres mix with the blood ejected from the left ventricle and are transported to the tissue in a similar pattern as red blood cells. The microspheres are trapped by the slightly smaller diameter capillaries ($8\mu$). The spheres remain lodged in the capillary bed with minimal migration until necropsy. To calibrate blood flow, an arterial blood flow sample was collected with a withdrawal rate of 2.06 ml/min during the time interval that the microspheres were infused. Following the determination of the areas at risk and the infarcted tissues, as described below, the left ventricular tissue slices were subdivided into epicardial, mid-myocardial, and endocardial thirds and the activity of each isotope was determined in a gamma counting system (Searl, Model 1185). Following this counting procedure, the tissue was divided into white, red and blue regions and recounted. The cardiac output and regional myocardial blood flow was calculated for each time point as previously described (Heyman, et al., "Blood flow measurement with radionuclide-labeled particles", *Progress in Cardiovascular Disease*, 20:55–79 (1977)).

Analysis of myocardium at risk. Immediately after the heart was removed, the first obtuse marginal branch of the circumflex coronary artery was isolated and cannulated. In addition, the left main coronary artery was cannulated to allow perfusion of both the left anterior descending and circumflex coronary arteries. Both vessels were simultaneously perfused at 120 mmHg. The marginal branch was perfused with 1.0% triphenyltetrazolium chloride (Sigma) and the left main coronary artery was perfused with 0.05% monastral blue. Triphenlytetrazolium chloride stains viable myocardium red and does not stain areas of necrotic or infarcted tissue. The heart was incubated in saline at 37° C. for 20 minutes to allow staining. The heart was then perfusion fixed with formalin. The mean total weight of the left ventricle was comparable for the DCLHb and HSA groups, 55.3±2.3 and 53.1±5.2 grams, respectively.

The heart was sectioned into 0.5 cm thick transverse slices with a mechanical slicer and each slice was weighed. The basilar surface of each slice was photographed. Each photograph was scanned into a MacIntosh computer (Scanjet scanner, Adobe photoshop program) and, using a computer-aided planimetric program (NIH Image), the area at risk and the area of infarction were quantitated. The area of infarction was expressed as a percent of the area at risk.

Data Analysis. Data are presented as mean values±SEM. Differences between groups at single time points were evaluated by the Student's t-test for unpaired data. For groups with significant disparities between standard deviations, nonparametric Mann-Whitney U-statistical analysis was performed. Differences among groups and between groups for multiple data points were compared by analysis of variance. The 0.05 level of significance was used to evaluate the statistical differences.

Hemodynamic Data. Heart rate and mean arterial blood pressure (MAP) remained constant during the first ninety five minutes of the experiment for both DCLHb and HSA treated groups (Table 1). Pigs receiving HSA showed a significant decrease in MAP at the 3 hour reperfusion period. Heart rate showed a significant 30% decrease from control in the DCLHb group at the 3 hour time point. Cardiac output was not significantly different from control during the occlusion or 5 minute reperfusion periods, but was significantly reduced in both the DCLHb and HSA groups at the 3 hour reperfusion period. Cardiac output was not different between the DCLHb and HSA groups at any time point. Calculated total peripheral resistance (TPR) was not significantly different between the DCLHb and HSA groups at either the control or occlusion time intervals. However, the DCLHb group had a significant increase in TPR at 5 minutes and 3 hours of reperfusion.

TABLE 1

HEMODYNAMIC DATA

| | | Mean Arterial Blood Pressure, mmHg | Heart Rate beat/min | Cardiac Output liters/min | Total Peripheral Resistance |
|---|---|---|---|---|---|
| Control | DCLHB | 97 ± 7 | 130 ± 10 | 4.3 ± 0.5 | 24 ± 2 |
| | HSA | 93 ± 5 | 125 ± 14 | 5.0 ± 0.5 | 19 ± 2 |
| Occlusion | DCLHB | 95 ± 10 | 120 ± 14 | 3.4 ± 0.3 | 28 ± 2 |
| (80 min.) | HSA | 98 ± 7 | 111 ± 5 | 3.3 ± 0.3 | 29 ± 1 |
| 5 min. | DCLHB | 114 ± 8 | 127 ± 7 | 3.2 ± 0.3 | 38 ± 4*† |
| Reperfusion | HSA | 94 ± 7 | 106 ± 5 | 4.0 ± 0.3 | 26 ± 1 |
| 3 hrs. | DCLHB | 92 ± 9† | 91 ± 4*† | 2.5 ± 0.4* | 46 ± 8*† |
| Reperfusion | HSA | 74 ± 9* | 125 ± 20 | 3.0 ± 0.2* | 25 ± 4 |

Blood Data. Table 2 shows that arterial pH was not significantly different between any of the time periods in either group. Arterial pH was 7.51±0.01 with a range between 7.46 and 7.54. Although both $PCO_2$ and $PO_2$ remained very stable throughout the experiment, $PCO_2$ was significantly different from the HSA group at the 5 minute reperfusion sample interval in the DCLHb treated group. $PO_2$ in the DCLHb group was significantly increased above the HSA group at the occlusion time period.

TABLE 2

BLOOD GAS DATA

| | | pH | $PCO_2$ mmHg | $PO_2$ mmHg |
|---|---|---|---|---|
| Control | DCLHb | 7.49 ± .03 | 35 ± 3 | 110 ± 8 |
| | HSA | 7.5 ± .023 | 40 ± 4 | 89 ± 7 |
| Occlusion | DCLHb | 7.53 ± .02 | 32 ± 2 | 106 ± 4† |
| (80 min.) | HSA | 7.46 ± .02 | 43 ± 3 | 86 ± 6 |
| 5 min. | DCLHb | 7.52 ± .02 | 30 ± 2† | 99 ± 10 |
| Reperfusion | HSA | 7.5 ± .034 | 40 ± 2 | 83 ± 7 |
| 3 hrs. | DCLHb | 7.54 ± .03 | 32 ± 3 | 96 ± 14 |
| Reperfusion | HSA | 7.5 ± .041 | 37 ± 3 | 76 ± 8 |

NOTE FOR TABLE 2:
Values are means ± SEM.
*Indicates significant difference from control ($P > 0.05$).
†Indicates significant difference from HSA.

Figure 1B:
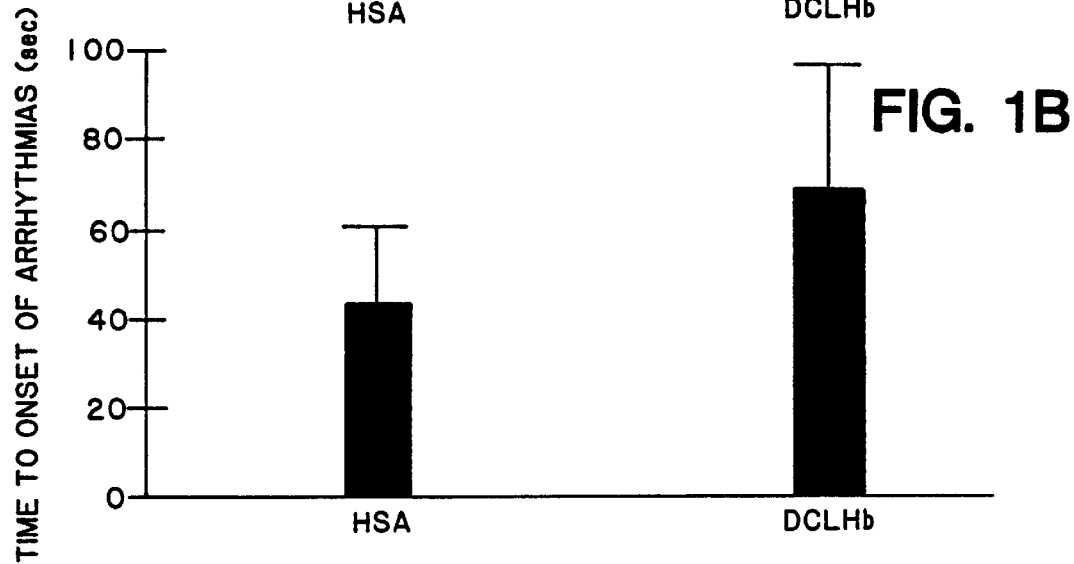
FIG. 1B. Effects of human serum albumin (HSA) and diaspirin cross-linked hemoglobin (DCLHb™) on the time to onset of reperfusion arrhythmias. The time in seconds is measured from beginning of reperfusion to the first series of reperfusion arrhythmias. Values are means±SEM.
Figure 1C:
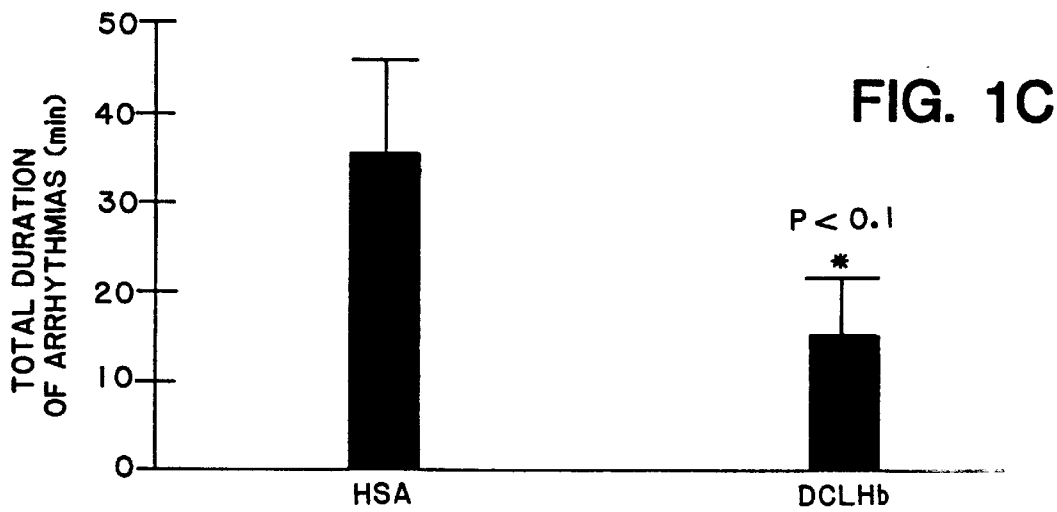
FIG. 1C. Effects of human serum albumin (HSA) and diaspirin cross-linked hemoglobin (DCLHb™) on the total duration of reperfusion arrhythmias. The time in minutes of arrhythmias are counted from beginning of the first accelerated idioventricular beat to a time when the arrhythmias occurred less than one every 30 seconds. Values are means±SEM. *Significantly different from HSA (P<0.10 ).
Figure 2:
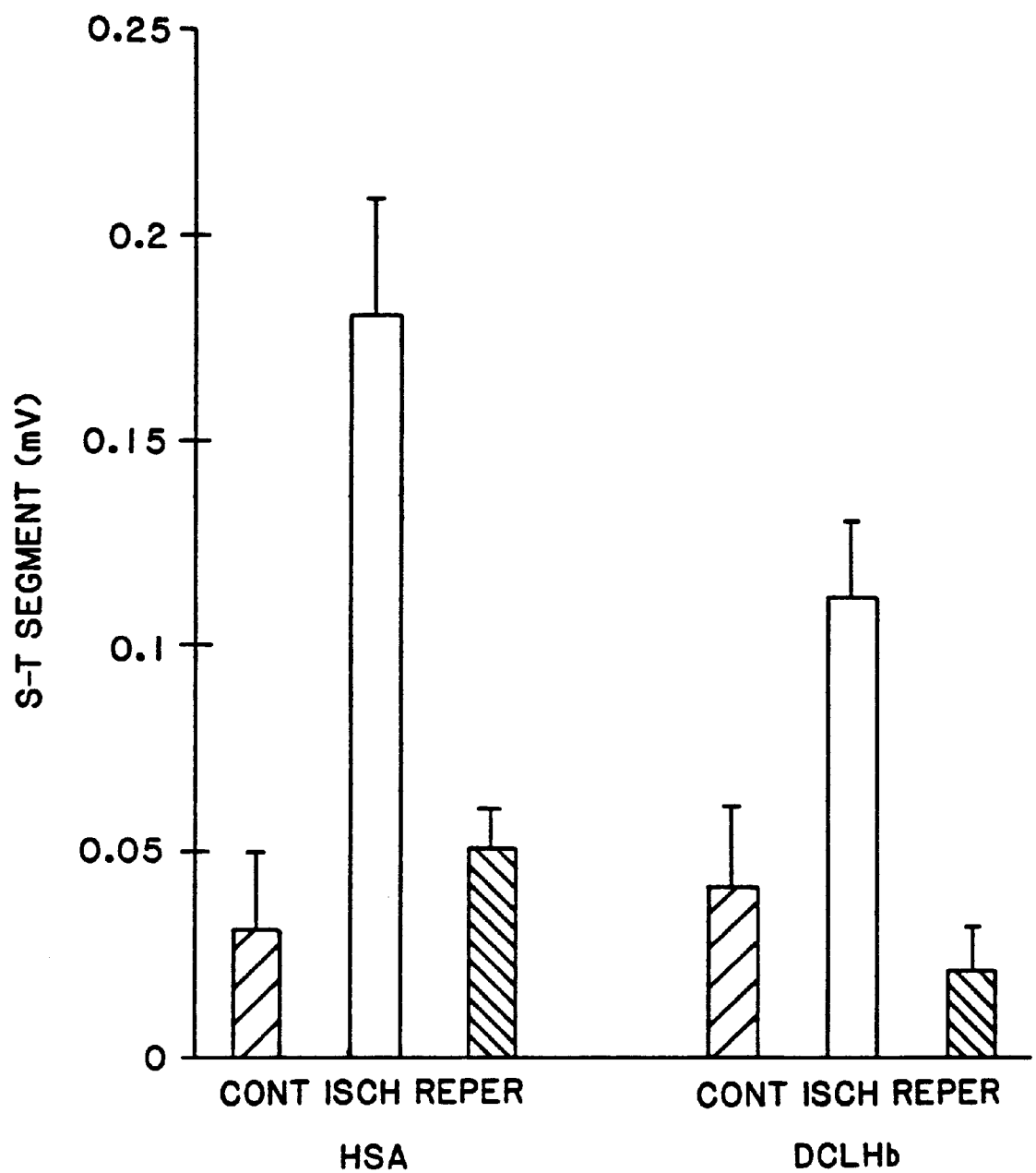
FIG. 2. S-T Segment changes (mVolts) in HSA and DCLHb treated groups. Control (Cont) is prior to balloon occlusion. Ischemia (Isch) is 80 minutes into ischemia prior to HSA or DCLHb infusion. Reperfusion is 3 hours into the reperfusion period.

ECG Data. Reperfusion arrhythmias were noted in both the DCLHb and HSA groups (FIG. 1); however, the total number of reperfusion arrhythmias, from start of reperfusion to 45 minutes post-reperfusion, was greater in the HSA group (1274±222) than the DCLHb group (437±198). The time to onset of arrhythmias (DCLHb, 67.5±28.4 seconds; HSA, 43.7±17.0 seconds) and the total duration of the arrhythmic period (DCLHb, 14.5±6.5 minutes; HSA, 35.2±10.9 minutes) were not statistically different for the two groups; however, there was a trend for DCLHb to increase the time to onset and to decrease the total duration of the arrhythmic period. Balloon occlusion produced a significant S-T segment elevation from control in both groups (DCLHb, 0.11±0.02 mV; HSA, 0.18±0.03 mV) (FIG. 2). There was no statistical difference between the two groups with regard to S-T segment elevation during the occlusion or 3 hour reperfusion time period. DCLHb had reduced the S-T segment elevation to 0.02±0.01 mV while the HSA treated animals still showed a 0.05±0.01 mV S-T segment change.

Table 3 shows a comparison of DCLHb infused animals with those either infused with HSA or nothing (control). With respect to both the number of arrhythmias detected and the length of time to onset of arrhythmias, the control (no treatment) most favorably compared to the HSA treated group.

TABLE 3

SWINE ISCHEMIA/REPERFUSION ECG DATA

| | | HSA | DCLHb | Control |
|---|---|---|---|---|
| Number of Arrhythmias | | 1274 ± 222 | 437 ± 198* | 1256 ± 434 |
| Duration of Arrhythmias (Minutes) | | 35 ± 11 | 14 ± 6 | 18 ± 6 |
| Time to Start of Arrhythmias (Seconds) | | 44 ± 17 | 67 ± 28 | 35 ± 15 |
| S-T | Baseline | 0.03 ± 0.02 | 0.04 ± 0.02 | 0.07 ± 0.01 |
| Segment | Ischemia | 0.18 ± 0.03 | 0.11 ± 0.02 | 0.36 ± 0.01* |
| Changes (mVolts) | Reperfusion | 0.05 ± 0.01 | 0.02 ± 0.01 | 0.02 ± 0.01 |

*Significantly different from other two treatment groups $p < 0.05$.

Blood Flow Data. Myocardial blood flow data are presented in Tables 4A and 4B. Table 4A shows blood flow to the epicardium, mid myocardium, endocardium and the endocardial:epicardial (endo/epi) blood flow ratio to an area of the free wall of the left ventricle that was not at risk for ischemia or infarction. We routinely examined tissue from the posterior wall of the left ventricle that was not perfused by the circumflex vessel. There were no differences in myocardial blood flow or endo/epi ratios with the exception of at the 3 hour reperfusion time interval in the DCLHb treated group, which exhibited a significant reduction in epicardial blood flow from control. Table 4B demonstrates the same parameters in tissue that is at risk for infarction. These blood flow measurements include tissue from both the ischemic area (white) and the area which was at risk but not ischemic (red). There was no significant difference between tissues of this region and the tissues in Table 4A during the control measurement period. The occlusion period produced a significant reduction in blood flow to all three regions of the myocardium in tissue at risk in pigs treated with either DCLHb or HSA. The endo/epi ratio was increased in both DCLHb and HSA groups during occlusion, indicating a proportionally greater reduction in blood flow to the epicardial region as compared to the endocardial layer of the myocardium. During the 5 minute reperfusion time period, there was a dramatic hyperemia to epi, mid, and endocardial tissue in both DCLHb and HSA groups with the exception of the endocardial region in the HSA group. The endo/epi ratio was therefore significantly less than that in the control group. Blood flows returned to control values at the 3 hour reperfusion period with the exception of the flow to the epicardial region in the DCLHb treated group. In this sample there was a significant difference in the pigs receiving DCLHb from control values and from the same tissue in the HSA treated group. Table 5 shows myocardial blood flow from the same hearts as included in Tables 4A and B, but this tissue has been divided into areas that were stained red (area at risk but not infarcted), tissues that were white (areas that did not take up the stain, therefore this area was infarcted) and the total combined flow to this region. Flow fell significantly to these regions during occlusion. The flow to the area at risk is defined as the collateral blood flow and was not significantly different between DCLHb and HSA. (See FIG. 3). Since this flow was measured prior to treatment, these two flows should be similar. During occlusion the infarcted area showed tissue flows that were not significantly different from zero. The 5 minute reperfusion data demonstrate significant active hyperemia to all tissues in both DCLHb and HSA treated groups and there was no difference between flows in the two groups. At the 3 hour time point, blood flow to both the area at risk and the infarcted tissue in the DCLHb treated group was significantly reduced from control values while the corresponding flows in HSA treated animals had returned to control values.

TABLE 4A

MYOCARDIAL BLOOD FLOW, ml/min/100 g
(Tissue Not in Area at Risk)

| | | EPI | MID | ENDO | ENDO/EPI |
|---|---|---|---|---|---|
| Control | DCLHb | 171 ± 31 | 195 ± 33 | 212 ± 38 | 1.3 ± 0.2 |
| | HSA | 143 ± 17 | 167 ± 19 | 180 ± 18 | 1.3 ± 0.1 |
| Occlusion (80 min.) | DCLHb | 135 ± 23 | 143 ± 21 | 160 ± 16 | 1.3 ± 0.1 |
| | HSA | 117 ± 16 | 144 ± 20 | 154 ± 20 | 1.3 ± 0.1 |
| 5 min. Reperfusion | DCLHb | 147 ± 18 | 188 ± 26 | 200 ± 22 | 1.4 ± 0.1 |
| | HSA | 139 ± 17 | 165 ± 19 | 174 ± 21 | 1.3 ± 0.1 |
| 3 hrs. Reperfusion | DCLHb | 89 ± 15* | 113 ± 20 | 130 ± 17 | 1.5 ± 0.1 |
| | HSA | 105 ± 18 | 126 ± 24 | 142 ± 26 | 1.4 ± 0.1 |

TABLE 4B

MYOCARDIAL BLOOD FLOW, ml/min/100 g
(Ischemic Tissue)

| | | EPI | MID | ENDO | ENDO/EPI |
|---|---|---|---|---|---|
| Control | DCLHb | 181 ± 28 | 188 ± 30 | 217 ± 39 | 1.2 ± 0.1 |
| | HSA | 152 ± 19 | 176 ± 23 | 202 ± 24 | 1.3 ± 0.1 |
| Occlusion (80 min.) | DCLHb | 81 ± 15* | 92 ± 19* | 121 ± 20* | 1.6 ± 0.1* |
| | HSA | 60 ± 14* | 78 ± 17* | 117 ± 22* | 2.1 ± 0.2* |
| 5 min. Reperfusion | DCLHb | 325 ± 29* | 308 ± 24* | 312 ± 29* | 1.0 ± 0.1 |
| | HSA | 301 ± 33* | 292 ± 42* | 268 ± 35 | 0.9 ± 0.1* |
| 3 hrs. Reperfusion | DCLHb | 95 ± 15*† | 102 ± 19 | 119 ± 18 | 1.3 ± 0.1 |
| | HSA | 157 ± 36 | 168 ± 37 | 179 ± 35 | 1.2 ± 0.2 |

TABLE 5

MYOCARDIAL BLOOD FLOW (ml/min/100 g) TO AREA
AT RISK AND AREA INFARCTED

| | | Area at Risk | Area Infarcted | TOTAL |
|---|---|---|---|---|
| Control | DCLHb | 242.09 ± 49.04 | 178.64 ± 37.20 | 210.78 ± 40.68 |
| | HSA | 234.95 ± 34.23 | 176.15 ± 32.42 | 203.30 ± 34.96 |
| Occlusion (80 min.) | DCLHb | 86.02 ± 10.89* | 2.45 ± 0.80* | 57.21 ± 12.05* |
| | HSA | 79.62 ± 16.55* | 9.94 ± 3.18* | 55.54 ± 14.57* |

TABLE 5-continued

MYOCARDIAL BLOOD FLOW (ml/min/100 g) TO AREA AT RISK AND AREA INFARCTED

|  |  | Area at Risk | Area Infarcted | TOTAL |
|---|---|---|---|---|
| 5 min. | DCLHb | 514.89 ± 90.85* | 390.79 ± 64.69* | 441.65 ± 70.75* |
| Reperfusion | HSA | 522.01 ± 71.64* | 313.84 ± 58.64* | 407.02 ± 64.50* |
| 3 hrs. | DCLHb | 121.29 ± 19.27*† | 102.86 ± 22.36* | 105.74 ± 13.93* |
| Reperfusion | HSA | 233.93 ± 49.06 | 166.00 ± 45.48 | 196.85 ± 48.27 |

NOTE FOR TABLE 5:
Values are means ± SEM.
*Indicates significant difference from control ($P < 0.05$).
†Indicates significant difference from HSA. Column one "Area at Risk" is total collateral blood flow during occlusion. Column two "Area Infarcted" is the area of no flow only. Column three is the flow to the entire area of infarction plus area at risk.

Table 6 demonstrates that in an anatomically paired organ, microspheres were equally distributed between the left and right kidney and that there was no significant difference between renal blood flow between the DCLHb and the HSA treated groups. These measurements are presented to validate the microsphere technique in this model.

TABLE 6

KIDNEY BLOOD FLOW (ml/min/100 g)

|  |  | LEFT | RIGHT | TOTAL |
|---|---|---|---|---|
| Control | DCLHb | 276 ± 53 | 292 ± 51 | 284 ± 51 |
|  | HSA | 330 ± 27 | 315 ± 34 | 323 ± 30 |
| Occlusion | DCLHb | 265 ± 34 | 278 ± 35 | 271 ± 34 |
| (80 min.) | HSA | 299 ± 07 | 291 ± 13 | 295 ± 09 |
| 5 min. | DCLHb | 237 ± 28 | 253 ± 25 | 244 ± 26 |
| Reperfusion | HSA | 331 ± 30 | 334 ± 30 | 338 ± 26 |
| 3 hrs. | DCLHb | 206 ± 29 | 223 ± 33 | 214 ± 30 |
| Reperfusion | HSA | 324 ± 46 | 311 ± 53 | 317 ± 48 |

NOTE FOR TABLE 6:
Values are means ± SEM. None of the values listed are different from control nor are there differences between treatment groups. There are no differences between right and left kidney flows.
LEFT = Left Kidney Flow,
RIGHT = Right Kidney Flow,
TOTAL = Total Kidney Flow.

Infarction Data. Infarct size and areas at risk in DCLHb and HSA treated hearts are shown in Table 7. The percent of the total left ventricle that was at risk was 14.6±2.6% for the DCLHb group and 10.6±2.1% for the HSA group. These values were not significantly different. The total area at risk was 1126±218 mm³ and 858±173 mm³ for DCLHb and HSA treated groups respectively. The total infarcted area for DCLHb was 326±91 mm³ and 456±101 mm³ for HSA. These data then yield the percent of infarcted tissue as compared to the area at risk. In the DCLHb group 30.9±6.1% of the area at risk was infarcted, while in the HSA group 53.2±1.9% of the area at risk was infarcted. Since this is a ratio, the data were subjected to an Arcsine transformation for the statistical analysis. The DCLHb group was statistically different from the HSA group at P<0.009 using an unpaired t-test.

Figure 3:
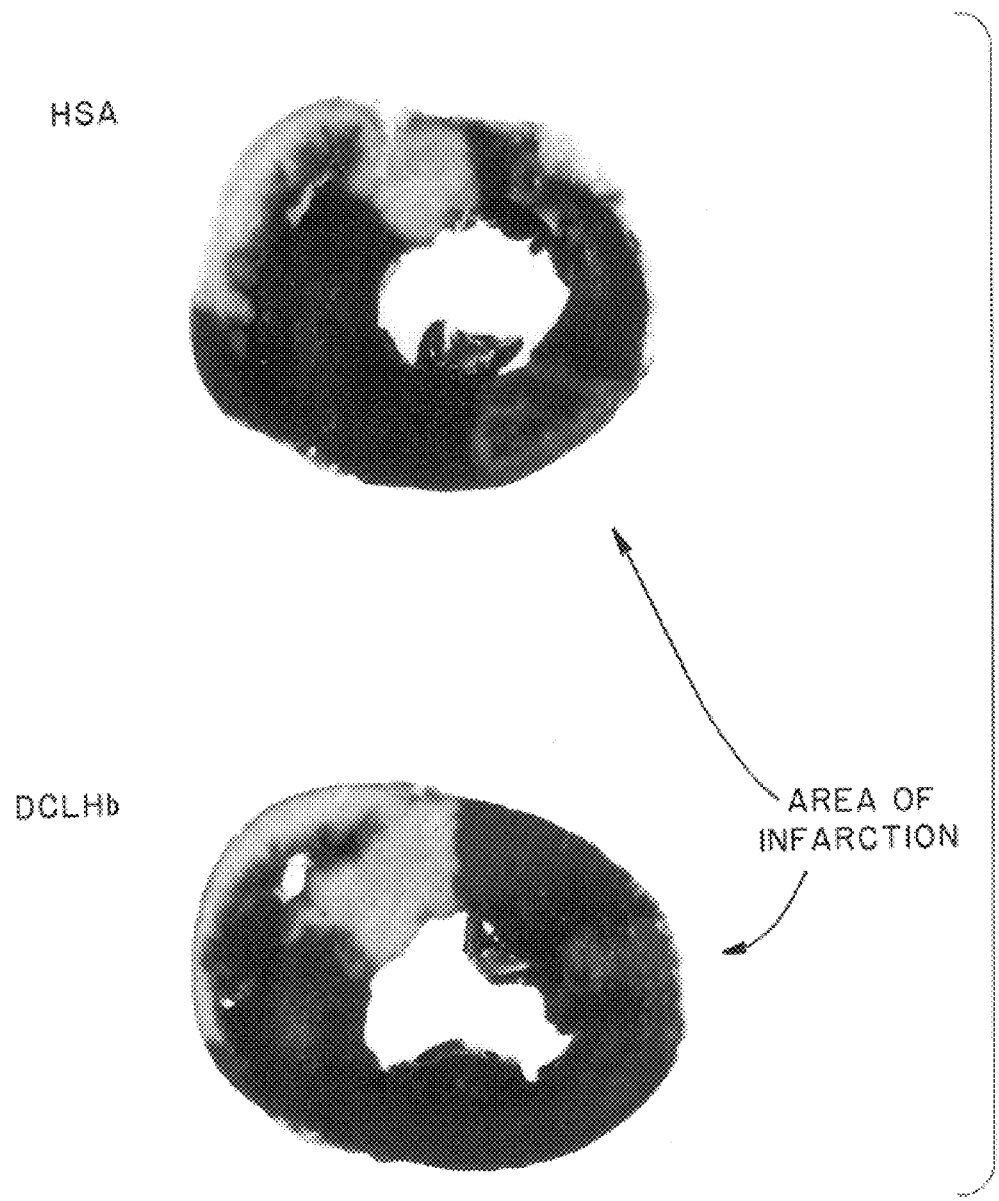
FIG. 3. Photograph comparing the infarct size in transverse cross-section between DCLHb and HSA infused test animals.

Intravenous infusion of DCLHb eighty minutes following occlusion of the first obtuse marginal branch of the circumflex coronary artery of the pig produced a significant reduction in the size of myocardial infarction compared to control animals which were infused with an oncotically matched human serum albumin solution. In addition, DCLHb significantly reduced detrimental reperfusion arrhythmias and produced a hemodynamically stable animal. FIG. 3 shows transverse tissue sections through the swine myocardium.

Comparison of the stained (vital) areas in the DCLHb and HSA perfused heart shows that the area of infarct is much smaller in the DCLHb perfused heart.

The myocardial blood flow data, as measured by radioactive microspheres, cannot account for the reduced infarction size in the DCLHb group. The only difference between the DCLHb and the HSA groups is the reduced epicardial blood flow and reduced blood flow to the area at risk in the DCLHb group at the 3 hour reperfusion time point. Reduction in flow at this time point should not correlate with an improvement in oxygen delivery and a reduction in infarction size.

TABLE 7

INFARCTION DATA

|  | % of LEFT VENTRICLE AT RISK | TOTAL AREA AT RISK mm³ | TOTAL AREA INFARCTED mm³ | % OF THE AREA AT RISK INFARCTED |
|---|---|---|---|---|
| DCLHb | 14.6 ± 2.6 | 1126 ± 218 | 326 ± 91 | 30.9 ± 6.1† |
| HSA | 10.6 ± 2.1 | 858 ± 173 | 456 ± 101 | 53.2 ± 1.9 |

NOTE FOR TABLE 7:
Values are means ± SEM.
†Indicates significant difference from HSA ($P < 0.05$).

EXAMPLE 2

The general procedures described in the experiments of Example 1 were repeated in another series of swine; however, the procedures were carried out under conditions of asepsis, so that the wounds could be closed, and the animals revived. The pigs were allowed to convalesce for a period of 21 days, and were then sacrificed. Table 8 shows the effect of infusing DCLHb and human serum albumin respectively, on reperfusion immediately after surgery, and at 21 days. The data show that hemoglobin infusion is highly correlated with maintenance of reperfusion and the absence of restenosis. Thus, the present invention provides a method of maintaining reperfusion to remote times, thereby reducing the incidence of restenosis of blood vessels in which a prior occlusion was relieved.

TABLE 8

21 DAY ISCHEMIA/REPERFUSION STUDY REPERFUSION RATE

| DATE | ANIMAL NO. | REPERFUSION AT 45 MIN. | REPERFUSION AT 21 DAYS |
|---|---|---|---|
| 03/05/94 | #359 DCLHb | ✓ | ✓ |
| 03/12/94 | #421 DCLHb | ? | ✓ |
| 05/10/94 | #371 DCLHb | Pig died before cath | |
| 08/11/94 | #548 DCLHb | ✓ | Pig died 5 days after cath |
| 08/30/94 | #586 DCLHb | ✓ | ✓ |
| 09/01/94 | #607 DCLHb | ✓ | ✓ |
| 09/20/94 | #652 DCLHb | ✓ | ✓ |
| 09/27/94 | #673 DCLHb | ✓ | ○ |
| TOTAL DCLHb ANIMALS | | 7/7 | 5/6 |
| 05/19/94 | #429 HSA | ✓ | ✓ |
| 05/26/94 | #430 HSA | ✓ | ✓ |
| 08/18/94 | #565 HSA | ✓ | Pig died after reperfusion |
| 08/23/94 | #585 HSA | ✓ | ✓ |
| 09/06/94 | #608 HSA | ○ | ○ |
| 09/08/94 | #628 HSA | ○ | ○ |
| 09/22/94 | #674 HSA | ○ | ○ |
| 10/04/94 | #684 HSA | ○ | ○ |
| 10/06/94 | #685 HSA | ✓ | ✓ |
| 10/13/94 | #1-95 HSA | ○ | ○ |
| 10/18/94 | #2-95 HSA | Pig died after giving HSA | |
| 10/20/94 | #5-95 HSA | ○ | Pig died following reperfusion |
| Total HSA Animals | | 5/11 | 4/9 |

✓ Indicates Reperfusion
○ Indicates No Reperfusion
? Indicates poor picture (unsure about reperfusion)

EXAMPLE 3

York swine of either sex, weighing 40–50 lbs., were surgically instrumented. Swine were initially sedated with Ketamine (10 mg/kg, i.m.) to allow placement of an intravenous catheter in the ear vein. Anesthesia was induced with sodium pentothal (10 mg/kg, i.v.). The trachea was intubated with a 6 or 7 mm endotracheal, and the animal was ventilated with a Harvard respirator and atelectasis was prevented with 3–5 cm $H_2O$ positive end expiratory pressure. A surgical plane of anesthesia was maintained with an infusion of sodium pentothal (1.2 mg/min). Mean arterial blood pressure and ECG were monitored continuously throughout the experiment. Under fluoroscopy, cardiac catheters were advanced to the appropriate locations. A 5F Pigtail catheter was advanced from the right femoral artery to the left ventricle. A control set of data was collected to include hemodynamic variables, blood gases, and cardiac output. A 9F sheath (Cordis) was placed in the left carotid artery and a 7F AR 2 guiding catheter was advanced to the left main coronary artery. A 0.014 inch floppy tip guide wire was advanced to the first obtuse marginal branch of the circumflex coronary artery and a Hartzler ACX coronary dilation catheter was advanced over the guide to a point just distal to the main circumflex artery. The coronary balloon catheter was inflated and remained inflated for 90 minutes. At 80 minutes of balloon inflation either DCLHb or HSA, 5 ml/kg, was infused at a rate of 1 ml/min/kg for five minutes. The balloon was deflated and the animal was observed for forty-five minutes of reperfusion. At this time the final data set was collected, and the pig was recovered from anesthesia.

Twenty-one days after the occlusion the pig was anesthetized in the same method as indicated above, and a coronary angiogram and a left ventriculogram was recorded in the 60° LAO position. Using a MedRad injector 25–40 ml of iodinated contrast (Renografin-76) was infused into the left ventricle at a flow rate of 15 ml/min. The heart was rapidly removed, the right ventricle trimmed off and the left ventricle sliced in 5 mm wide rings from the apex to the base, and each ring was placed into 4% phosphate buffered formaldehyde. Hearts were sent for microscopic analysis.

Figure 4:
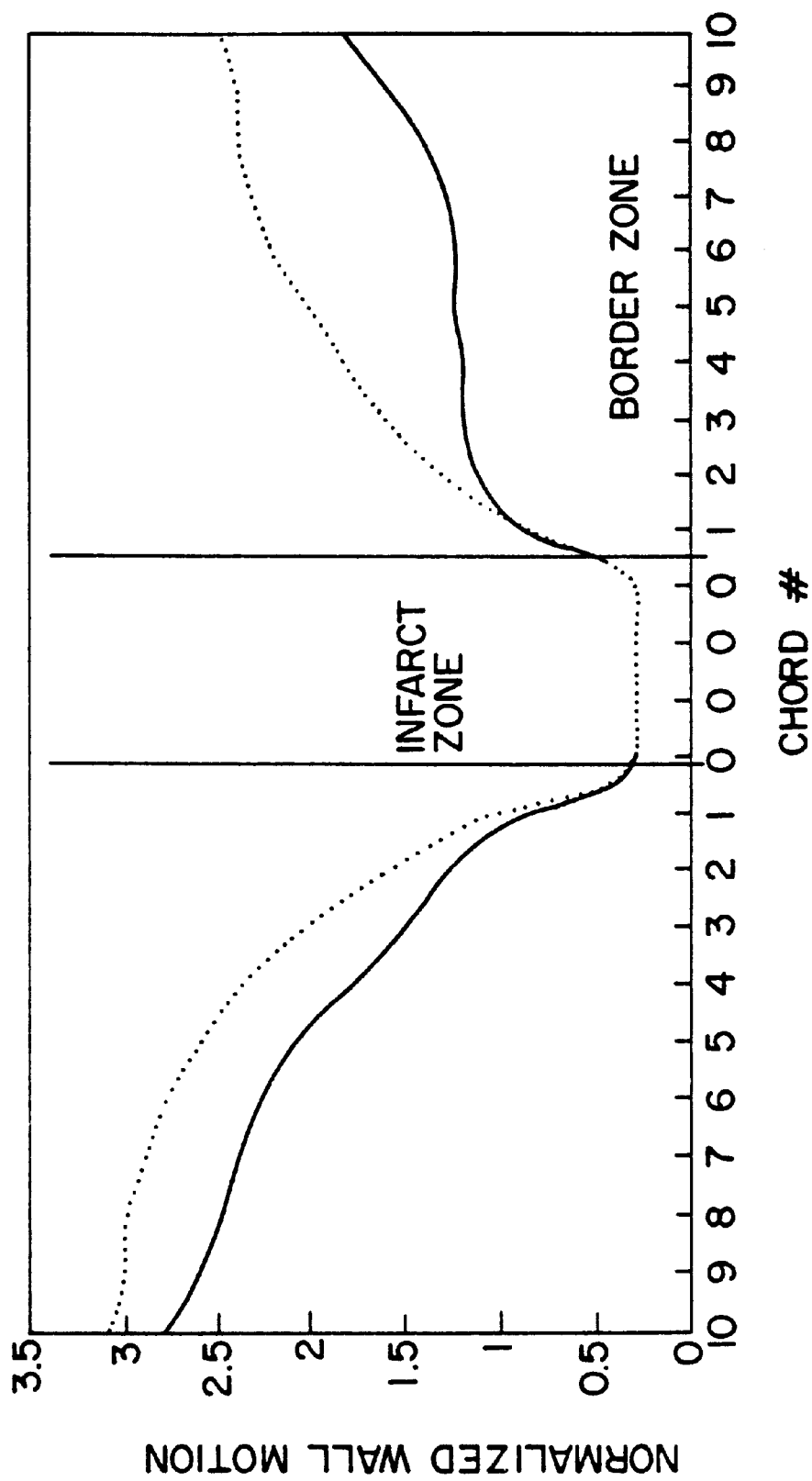
FIG. 4. Effects of DCLHb and HSA on cardiac wall motion.

The ventriculogram was analyzed using centerline analysis, Sheehan et al., Circulation, 74(2)293 (1986). Wall motion was measured along 100 chords constructed perpendicular to a centerline drawn midway between the end-diastolic and end-systolic contours, normalized for heart size and plotted as relative wall motion index units. Chords were compared to the region of infarction, akinetic and to the area of normal wall motion, eukinetic. We specifically focused on the border region between eukinetic and akinetic, which is defined as hypokinetic. The regions of akinesis and hypokinesis were compared to the infarct related artery in the coronary angiogram. The results are shown in FIG. 4, and show clearly an improvement in wall motion score of at least 0.15 relative index units in between the infarct zone and 20 chords in the tissue region at risk.

What is claimed is:

1. A method for reducing restenosis of a blood vessel, comprising systemically administering stroma-free, diaspirin-crosslinked hemoglobin to an ischemic patient at risk for developing restenosis.

2. The method of claim 1 wherein the patient at risk for restenosis is to undergo an angioplasty procedure.

3. The method of claim 1 wherein the patient at risk for restenosis is to undergo bypass surgery.

4. A method for reducing restenosis of a blood vessel, comprising systemically administering stroma-free hemoglobin to an ischemic patient at risk for developing restenosis, and removing a blockage in a blood vessel of the patient within one hour after administering the stroma-free hemoglobin.

5. A method for reducing restenosis of a blood vessel, comprising systemically administering from about 75 milligrams of stroma-free hemoglobin per kilogram body weight to about 750 milligrams of stroma-free hemoglobin per kilogram body weight to an ischemic patient at risk for developing restenosis.

6. A method for improving contractile function in ischemic cardiac tissue comprising systemically administering stroma-free hemoglobin to an ischemic patient, and removing a blockage in a cardiac blood vessel of the patient within one hour after administering the stroma-free hemoglobin to reestablish blood flow to the cardiac tissue.

7. A method for reducing the frequency, magnitude or duration of cardiac arrhythmias comprising systemically administering stroma-free hemoglobin to an ischemic patient, and removing a blockage in a blood vessel of the patient within one hour after administering the stroma-free hemoglobin to reestablish blood flow within the blood vessel.

8. The method of claim 4 wherein the stroma-free hemoglobin is a physiologically acceptable solution containing from about 75 milligrams hemoglobin per kilogram body weight to about 750 milligrams hemoglobin per kilogram body weight.

9. The method of claim 6 wherein the stroma-free hemoglobin is a physiologically acceptable solution containing from about 75 milligrams hemoglobin per kilogram body weight to about 750 milligrams hemoglobin per kilogram body weight.

10. The method of claim 7 wherein the stroma-free hemoglobin is a physiologically acceptable solution containing from about 75 milligrams hemoglobin per kilogram body weight to about 750 milligrams hemoglobin per kilogram body weight.

11. The method of claim 4 wherein the stroma-free hemoglobin is administered within twenty minutes before removing a blockage in a blood vessel of the patient.

12. The method of claim 1 wherein the patient is a human.

13. The method of claim 1 wherein the stroma-free hemoglobin is a physiologically acceptable solution containing from about 10 milligrams hemoglobin per kilogram body weight to about 2,500 milligrams hemoglobin per kilogram body weight.

14. A method for reducing restenosis of a blood vessel, comprising systemically administering stroma-free hemoglobin to an ischemic patient at risk for developing restenosis, and removing a blockage in a blood vessel of the patient after administering the stroma-free hemoglobin.

15. The method of claim 14 wherein the patient at risk for restenosis is to undergo an angioplasty procedure.

16. The method of claim 14 wherein the patient at risk for restenosis is to undergo bypass surgery.

17. The method of claim 14 wherein the patient is a human.

18. The method of claim 14 wherein the stroma-free hemoglobin is selected from the group consisting of crosslinked hemoglobin and polymerized hemoglobin.

19. The method of claim 18 wherein the crosslinked hemoglobin is diaspirin-crosslinked hemoglobin.

20. The method of claim 14 wherein the stroma-free hemoglobin is a physiologically acceptable solution containing from about 10 milligrams hemoglobin per kilogram body weight to about 2,500 milligrams hemoglobin per kilogram body weight.

21. The method of claim 14 wherein the stroma-free hemoglobin is a physiologically acceptable solution containing from about 75 milligrams hemoglobin per kilogram body weight to about 750 milligrams hemoglobin per kilogram body weight.

22. A method for improving contractile function in ischemic cardiac tissue comprising systemically stroma-free hemoglobin to an ischemic patient, and removing a blockage in a cardiac blood vessel of the patient after administering the stroma-free hemoglobin to reestablish blood flow to the cardiac tissue.

23. The method of claim 6 wherein the stroma-free hemoglobin is administered within twenty minutes before removing the blockage.

24. The method of claim 22 wherein the patient is a human.

25. The method of claim 22 wherein the stroma-free hemoglobin is selected from the group consisting of crosslinked hemoglobin and polymerized hemoglobin.

26. The method of claim 25 wherein the crosslinked hemoglobin is diaspirin-crosslinked hemoglobin.

27. The method of claim 22 wherein the stroma-free hemoglobin is a physiologically acceptable solution containing from about 10 milligrams hemoglobin per kilogram body weight to about 2,500 milligrams hemoglobin per kilogram body weight.

28. The method of claim 22 wherein the stroma-free hemoglobin is a physiologically acceptable solution containing from about 75 milligrams hemoglobin per kilogram body weight to about 750 milligrams hemoglobin per kilogram body weight.

29. A method for reducing the frequency, magnitude or duration of cardiac arrhythmias comprising systemically administering stroma-free hemoglobin to an ischemic patient, and removing a blockage in a blood vessel of the patient after administering the stroma-free hemoglobin to reestablish blood flow within the blood vessel.

30. The method of claim 7 wherein the stroma-free hemoglobin is administered within twenty minutes before removing the blockage.

31. The method of claim 29 wherein the patient is a human.

32. The method of claim 29 wherein the stroma-free hemoglobin is selected from the group consisting of crosslinked hemoglobin and polymerized hemoglobin.

33. The method of claim 32 wherein the crosslinked hemoglobin is diaspirin-crosslinked hemoglobin.

34. The method of claim 29 wherein the stroma-free hemoglobin is a physiologically acceptable solution containing from about 10 milligrams hemoglobin per kilogram body weight to about 2,500 milligrams hemoglobin per kilogram body weight.

35. The method of claim 29 wherein the stroma-free hemoglobin is a physiologically acceptable solution containing from about 75 milligrams hemoglobin per kilogram body weight to about 750 milligrams hemoglobin per kilogram body weight.

* * * * *